US012661107B2

(12) United States Patent
Curtis et al.

(10) Patent No.: US 12,661,107 B2
(45) Date of Patent: Jun. 23, 2026

(54) METHODS FOR ATTACHING TISSUE TO BONE UTILIZING A SCAFFOLD

(71) Applicant: AEVUMED, INC., Malvern, PA (US)

(72) Inventors: Miles Curtis, Philadelphia, PA (US); Saif Khalil, Malvern, PA (US); Robert P. Douglass, Bryn Mawr, PA (US)

(73) Assignee: AEVUMED, INC., Malvern, PA (US)

( * ) Notice: Subject to any disclaimer, the term of this patent is extended or adjusted under 35 U.S.C. 154(b) by 102 days.

(21) Appl. No.: 18/492,828

(22) Filed: Oct. 24, 2023

(65) Prior Publication Data

US 2024/0130722 A1 Apr. 25, 2024
US 2024/0225632 A9 Jul. 11, 2024

Related U.S. Application Data

(60) Provisional application No. 63/380,840, filed on Oct. 25, 2022.

(51) Int. Cl.
*A61B 17/04* (2006.01)
*A61F 2/08* (2006.01)

(52) U.S. Cl.
CPC .. *A61B 17/0401* (2013.01); *A61F 2002/0852* (2013.01)

(58) Field of Classification Search
CPC . A61B 17/0401; A61B 17/04; A61B 17/0466; A61B 2017/0495; A61B 2017/0464; A61B 2017/0404; A61B 2017/0406; A61B 2/0811; A61F 2002/0888
See application file for complete search history.

(56) References Cited

U.S. PATENT DOCUMENTS

2012/0265219 A1* 10/2012 Rushdy .............. A61B 17/0401
606/139
2017/0216016 A1* 8/2017 Sengun ................ A61F 2/0811
2018/0263755 A1* 9/2018 Adams ............... A61B 17/0401

* cited by examiner

*Primary Examiner* — Katherine M Shi
(74) *Attorney, Agent, or Firm* — Riverside Law LLP

(57) ABSTRACT

A method for attaching tissue to bone includes the steps of inserting a first anchor into bone, advancing a first limb of a first suture from the first anchor through the tissue and a scaffold, and advancing a second limb of the first suture from the first anchor though the tissue. Alternate methods for attaching tissue to bone are also disclosed.

31 Claims, 13 Drawing Sheets

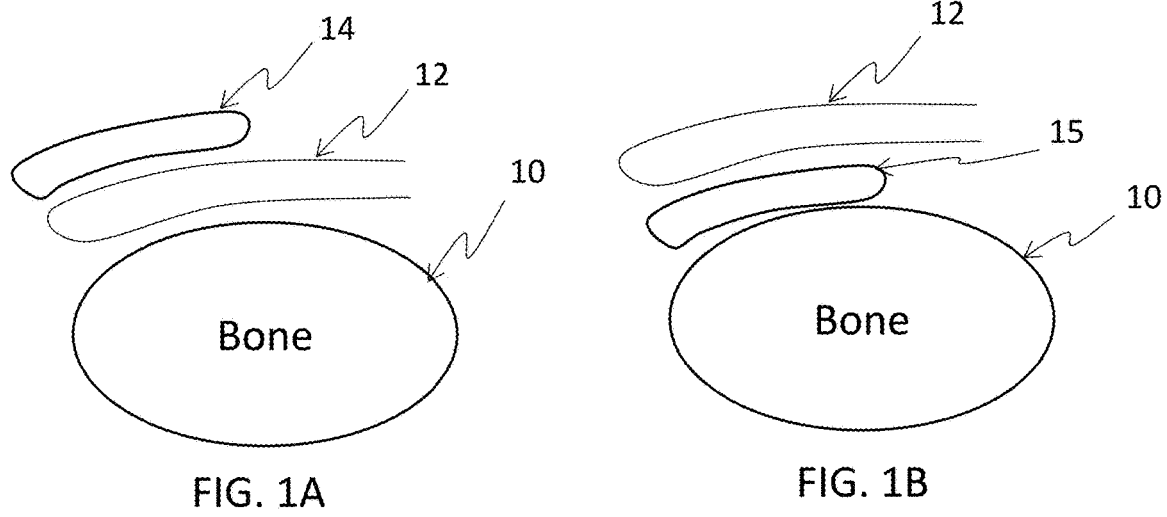
FIG. 1A
FIG. 1B
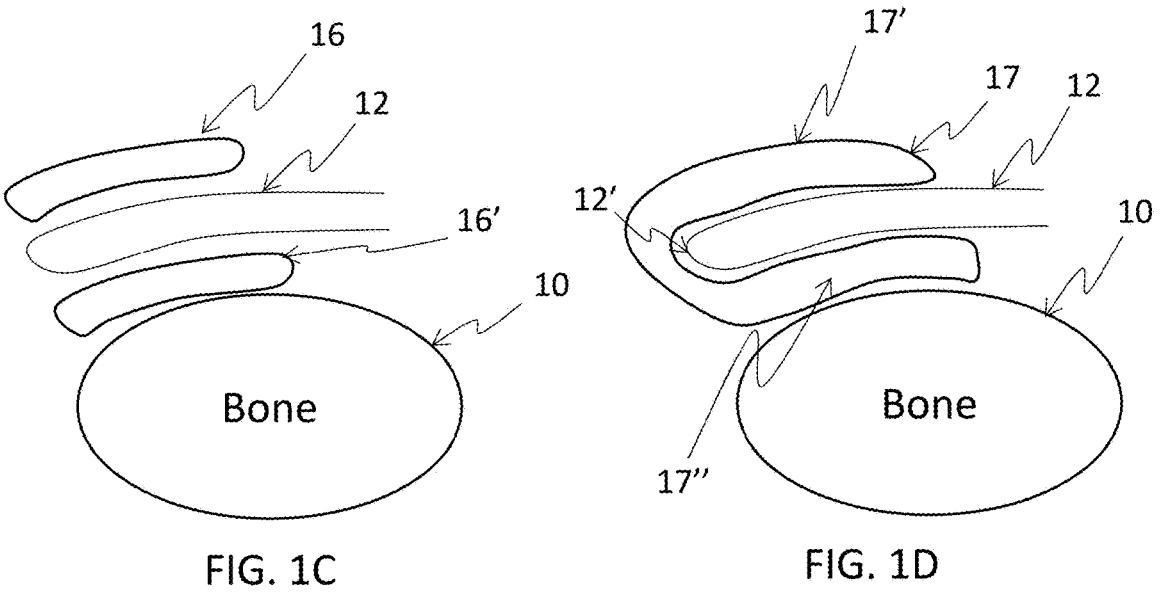
FIG. 1C
FIG. 1D

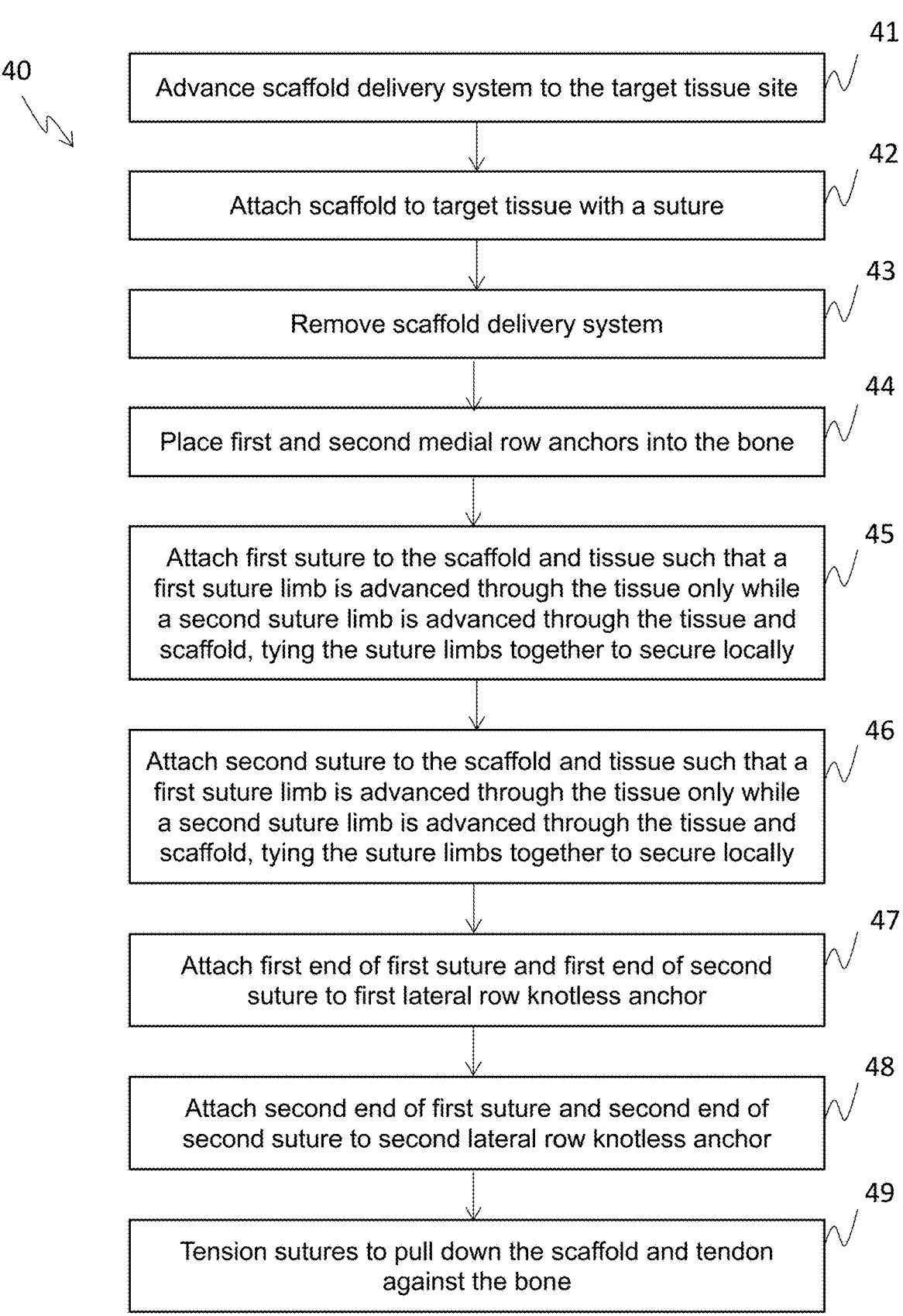

40

41
Advance scaffold delivery system to the target tissue site

42
Attach scaffold to target tissue with a suture

43
Remove scaffold delivery system

44
Place first and second medial row anchors into the bone

45
Attach first suture to the scaffold and tissue such that a first suture limb is advanced through the tissue only while a second suture limb is advanced through the tissue and scaffold, tying the suture limbs together to secure locally 46
Attach second suture to the scaffold and tissue such that a first suture limb is advanced through the tissue only while a second suture limb is advanced through the tissue and scaffold, tying the suture limbs together to secure locally 47
Attach first end of first suture and first end of second suture to first lateral row knotless anchor 48
Attach second end of first suture and second end of second suture to second lateral row knotless anchor 49
Tension sutures to pull down the scaffold and tendon against the bone

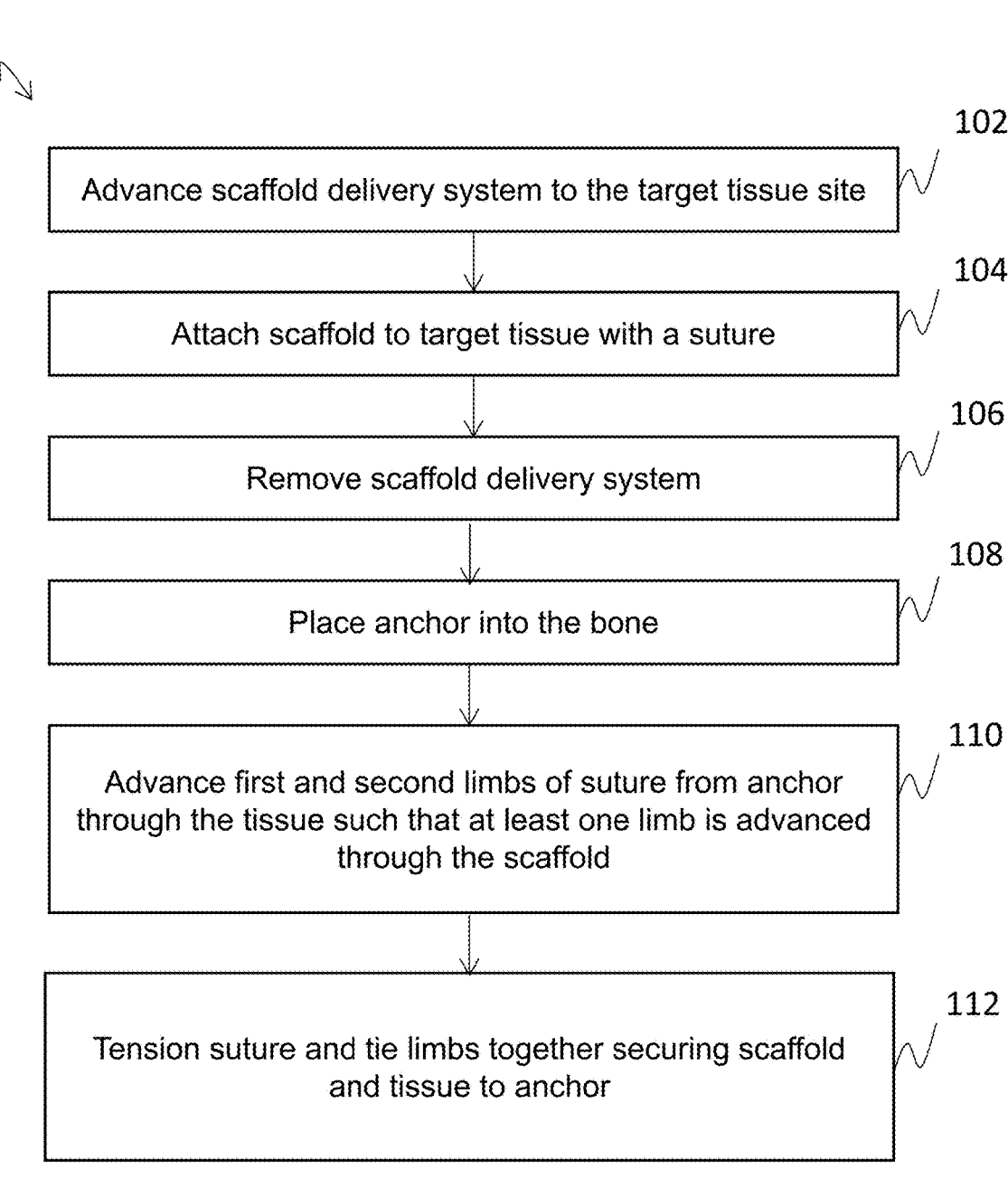

102

Advance scaffold delivery system to the target tissue site

104

Attach scaffold to target tissue with a suture

106

Remove scaffold delivery system

108

Place anchor into the bone

110

Advance first and second limbs of suture from anchor through the tissue such that at least one limb is advanced through the scaffold

112

Tension suture and tie limbs together securing scaffold and tissue to anchor

Insert a first anchor into bone

204

Advance a first limb of a first suture from the first anchor
through the tissue and a scaffold

206

Advance a second limb of the first suture from the first
anchor though the tissue

300

302

Insert a plurality of anchors into bone

304

Advance at least one limb of at least one suture from at least one of the plurality of anchors through the tissue and a scaffold

306

Connect each of the plurality of anchors to at least one suture limb that advances through the tissue and connects to at least one other anchor of the plurality of anchors

500

502
Insert a first anchor into bone

504
Advance a first limb of a first suture through the tissue and a scaffold

506
Advance a second limb of the first suture though the tissue

508
Knot the first and second limb above the scaffold

508
Attach a first and second free end of the knotted suture to an anchor

METHODS FOR ATTACHING TISSUE TO BONE UTILIZING A SCAFFOLD

CROSS-REFERENCE TO RELATED APPLICATIONS

This application claims priority to U.S. provisional application No. 63/380,840 filed Oct. 25, 2022, incorporated herein by reference in its entirety.

BACKGROUND OF THE INVENTION

Soft tissue tears are common and fasteners alone are inadequate for proper healing. As the soft tissue is in a weakened state, penetrating the soft tissue with the fasteners merely introduces additional weak points that are prone to further tearing.

Scaffold and suture anchoring devices for attaching scaffolds and soft tissue to bone have been described to enhance repair and healing. For example, US Patent Publication No. US 2022/0287707 to Khalil et al., incorporated herein by reference in its entirety, describes a device that includes a retainer mechanism that holds the scaffolds in a grasper to be actuated to release the scaffolds from the grasper. The device may include retractable needles that can be actuated to pass suture threads through the grasper to anchor scaffolds to a target site. Depending on various criteria including the anatomy of the patient, nature of the tissue tear, bone area for attachment, skill of the practitioner and types of anchors available, improved methods of treatment for attaching tissue to bone when using a scaffold would benefit the art and improve tissue tear treatment strategies.

Embodiments described herein include improved methods of using a scaffold for attaching soft tissue to bone.

SUMMARY OF THE INVENTION

In one embodiment, a method for attaching tissue to bone includes the steps of inserting a first anchor into bone; advancing a first limb of a first suture from the first anchor through the tissue and a scaffold; and advancing a second limb of the first suture from the first anchor though the tissue. In one embodiment, the second limb of the first suture is not advanced through the scaffold. In one embodiment, the second limb of the first suture is advanced through the scaffold. In one embodiment, the first and second limb of the first suture are knotted above the scaffold. In one embodiment, the first anchor is positioned interior to a footprint of the scaffold. In one embodiment, the first anchor is positioned exterior to a footprint of the scaffold. In one embodiment, the first anchor is positioned traversing an edge of the scaffold. In one embodiment, the method includes the steps of inserting a second anchor into bone; advancing a first limb of a second suture from the second anchor through the tissue and the scaffold; and advancing a second limb of the second suture from the second anchor though the tissue. In one embodiment, the second limb of the second suture is not advanced through the scaffold. In one embodiment, the second limb of the second suture is advanced through the scaffold. In one embodiment, the first and second limb of the second suture are knotted above the scaffold. In one embodiment, the second anchor is positioned interior to a footprint of the scaffold. In one embodiment, the second anchor is positioned exterior to a footprint of the scaffold. In one embodiment, the second anchor is positioned traversing an edge of the scaffold. In one embodiment, the scaffold is positioned above the tissue. In one embodiment, the scaffold is positioned below the tissue. In one embodiment, the scaffold wraps around a tip of the issue and is positioned both above and below the tissue.

In one embodiment, a method for attaching tissue to bone includes the steps of inserting a plurality of anchors into bone; advancing at least one limb of at least one suture from at least one of the plurality of anchors through the tissue and a scaffold; and connecting each of the plurality of anchors to at least one suture limb that advances through the tissue and connects to at least one other anchor of the plurality of anchors.

In one embodiment, a method for attaching tissue to bone includes the steps of inserting a first and second anchor into bone; advancing a first limb of a first suture from the first anchor through the tissue; advancing a first limb of a second suture from the second anchor though the tissue; and knotting the first limb of the first suture and the first limb of the second suture above a scaffold. In one embodiment, the first limb of the first suture and the first limb of the second suture do not advance through the scaffold.

In one embodiment, a method for attaching tissue to bone includes the steps of inserting a first anchor into bone; advancing a first limb of a first suture through the tissue and a scaffold; advancing a second limb of the first suture though the tissue; knotting the first and second limb above the scaffold; and attaching a first and second free end of the knotted suture to an anchor. In one embodiment, the first and second free end of the knotted suture are attached to the same anchor. In one embodiment, the first and second free end of the knotted suture are attached different anchors.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIGS. 1A through 1D are diagrams of scaffold attachment configurations according to one embodiment, including the scaffold above the tissue (FIG. 1A), below the tissue (FIG. 1B), above and below the tissue (FIG. 1C), and wrapped around a tip of the tissue (FIG. 1D).

FIG. 3 is a flow chart of a method for attaching tissue to bone according to one embodiment.

DETAILED DESCRIPTION OF THE INVENTION

Figure 2A:
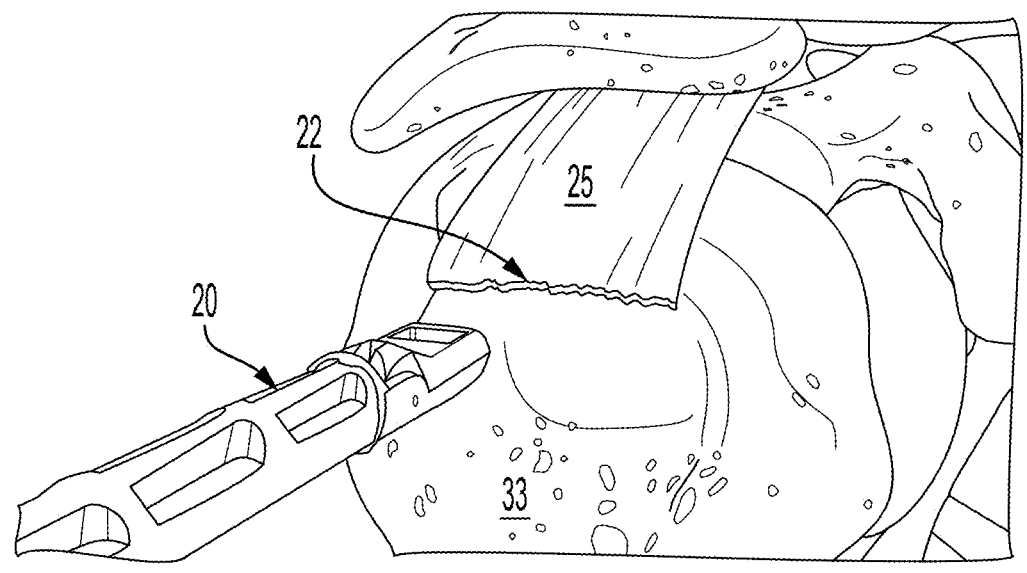
FIGS. 2A through 2H are procedural views of a method attaching tissue to bone, in this example attaching tendon to bone as described by the steps outlined in the flow chart of FIG. 2J according to one embodiment.
Figure 2B:
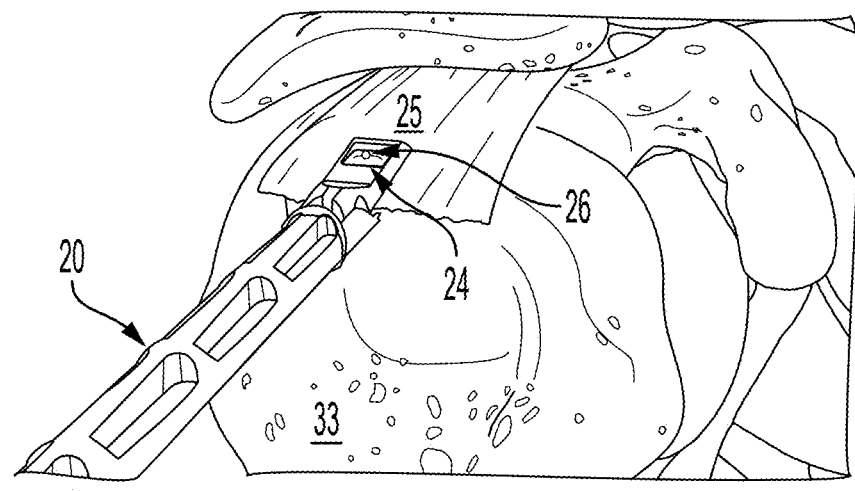
Figure 2C:
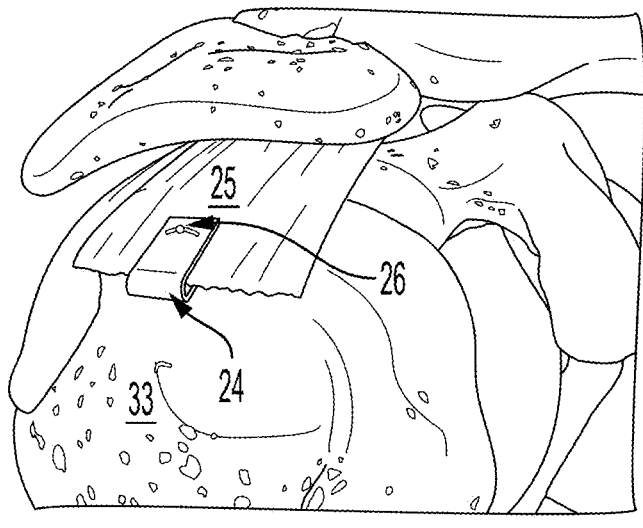
Figure 2D:
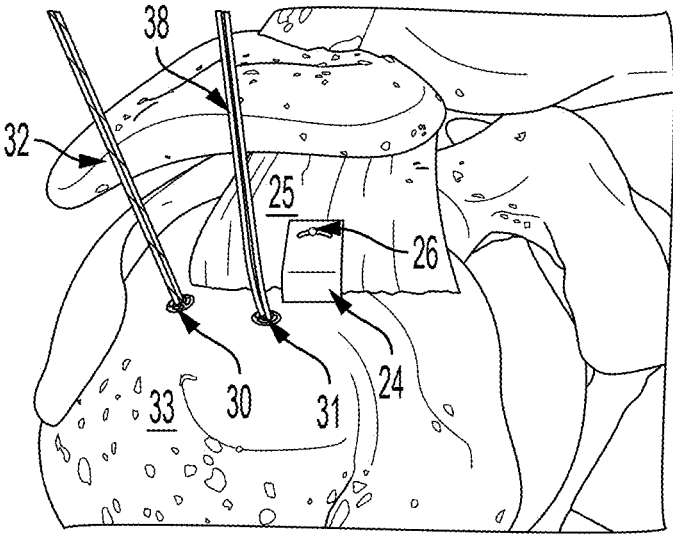
Figure 2E:
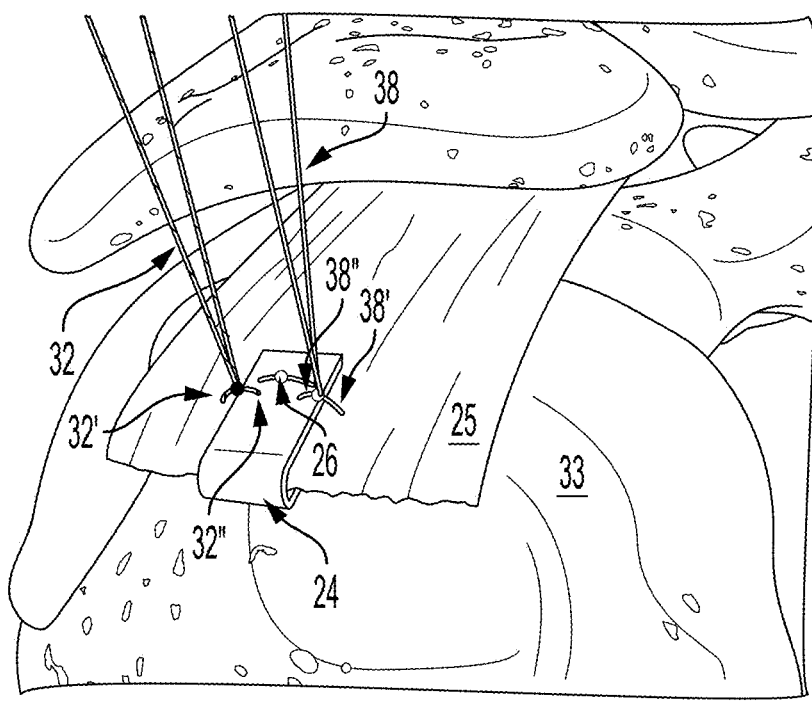
Figure 2F:
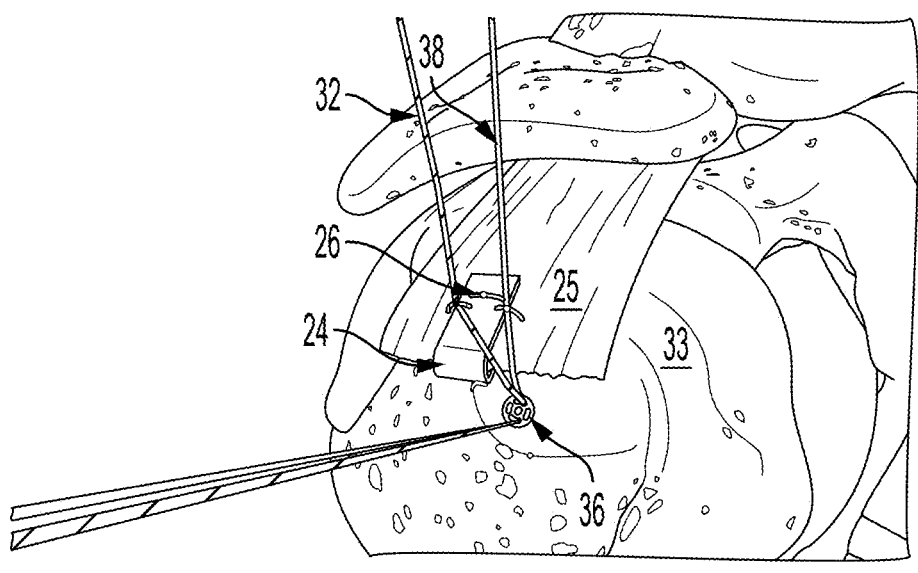
Figure 2G:
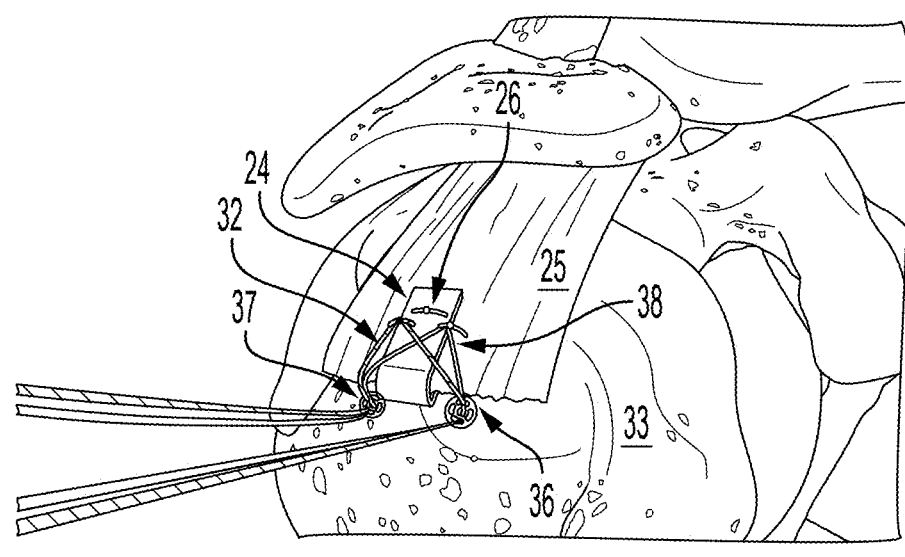

It is to be understood that the figures and descriptions of the present invention have been simplified to illustrate elements that are relevant for a more clear comprehension of the present invention, while eliminating, for the purpose of clarity, many other elements found in systems and methods of attaching tissue to bone using a scaffold. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are methods attaching tissue to bone using a scaffold.

With reference to FIGS. 1A-1D, scaffold attachment configurations are shown according to several embodiments. For purposes of using a scaffold to reinforce weak points that are prone to further tearing, several different configurations can be implemented. FIG. 1A shows an onlay arrangement with the scaffold 14 disposed above the tendon 12 such that the tendon 12 is positioned between the scaffold 14 and the bone 10. FIG. 1B shows an underlay arrangement with the scaffold 15 disposed below the tendon 12 such that scaffold 15 is positioned between the tendon 12 and the bone 10. FIG. 1C shows a combined onlay and overlay arrangement with a first scaffold 16 disposed above the tendon 12 and a separate second scaffold 16' positioned below the tendon 12, such that the tendon 12 is positioned between the first scaffold 16 and the second scaffold 16' while the second scaffold 16' is positioned between the tendon 12 and the bone 10. FIG. 1D shows a wrap-around arrangement with a single contiguous scaffold 17 disposed above and below the tendon 12 by wrapping around the tip 12' of the tendon 12 such that the tendon 12 is positioned between first and second ends 17', 17" of the scaffold 17 while the second end 17" of the scaffold is disposed between the tendon 12 and the bone 10. Embodiments described below can be implemented with these various scaffold attachment configurations.

Figure 2H:
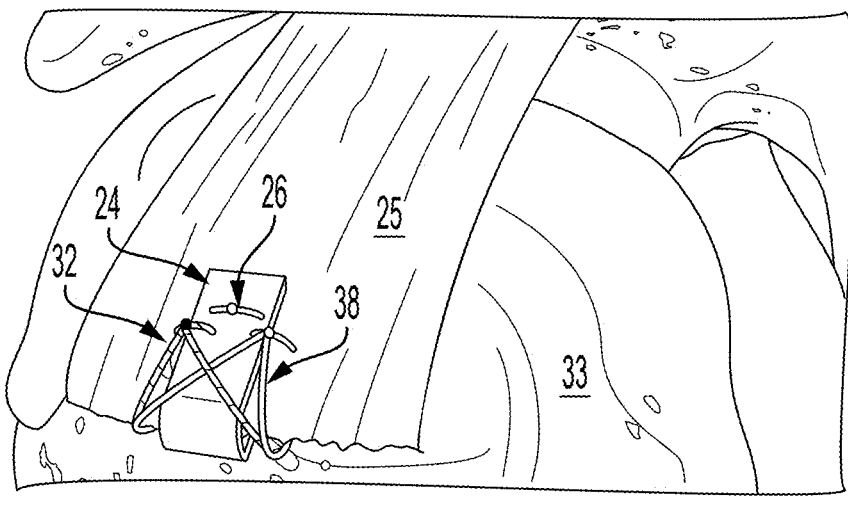

With reference now to FIGS. 2A-2H, a method 40 for attaching tissue to bone using a scaffold is shown according to one embodiment. The method 40 includes the steps of advancing the scaffold delivery system 20 to the target tissue site 22, 41 (FIG. 2A), attaching the scaffold 24 to the target tissue site with a suture 26, 42 (FIG. 2B), removing the scaffold delivery system 43 (FIG. 2C), placing first and second medial row anchors 30, 31 into the bone 50, 44 (FIG. 2D), attaching the first suture 32 connected to the first medial row anchor 30 to the scaffold 24 and tissue 25 such that a first suture limb 32' of the first suture 32 is advanced through the tissue 25 only while a second suture limb 32" of the first suture 32 is advanced through the tissue 25 and scaffold 24, tying the suture limbs 32', 32" together to secure locally against the first medial row anchor 30, 45 (FIG. 2E), and attaching the second suture 38 connected to the second medial row anchor 31 to the scaffold 24 and tissue 25 such that a first suture limb 38' of the second suture 38 is advanced through the tissue 25 only while a second suture limb 38" of the second suture 38 is advanced through the tissue 25 and scaffold 25, tying the suture limbs 38', 38" together to secure locally against the second medial row anchor 31, 46 (FIG. 2E), attaching a first end of the first suture 32 and a first end of the second suture 38 to a first lateral row knotless anchor 36, 47 (FIG. 2F), attaching a second end of the first suture 32 and a second end of the second suture 38 to a second lateral row knotless anchor 37, 48 (FIG. 2G), and tensioning the sutures 32, 38 to pull down the scaffold 24 and tissue 25 against the bone 33, 49 (FIG. 2H). In one embodiment, both suture limbs can be passed though the scaffold from the anchor instead of just one. In one embodiment, a single suture limb is passed though the scaffold from an anchor.

In one embodiment, a single anchor and a single suture is used, where at least one limb of the single suture is advanced from the anchor though the scaffold. With reference now to FIG. 3, according to one embodiment, a method 100 for attaching tissue to bone using a scaffold includes the steps of advancing scaffold delivery system to the target tissue site 102, attaching the scaffold to target tissue with a suture 104, removing the scaffold delivery system 106, placing an anchor into the bone 108, advancing first and second limbs of a suture from the anchor through the tissue such that at least one limb is advanced through the scaffold 110, and tensioning the suture and tying the limbs together, securing scaffold and tissue to anchor 112. As with other embodiments, although a single suture limb through the scaffold can be relied upon for anchoring the scaffold and tissue to bone, both suture limbs can be advanced through the scaffold.

Figure 4A:
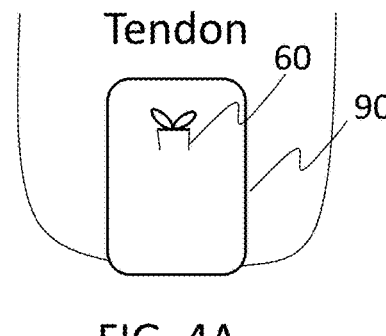
FIGS. 4A through 4J depict various configurations for attaching tissue to bone according to various embodiments.
Figure 4B:
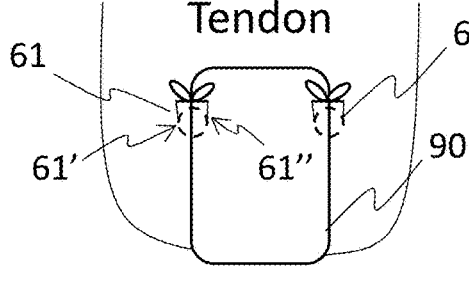

With reference to FIGS. 4A-4J, various embodiments for attaching tissue to bone are shown. As shown in FIG. 4A, the scaffold 90 can attach to the tissue by placement of a suture 60, for example using the delivery system described in previous embodiments. The scaffold 90 configuration is depicted as a wrapped around a tip of the tissue, however as described above can alternatively be positioned above the tissue only, below the tissue only, or two separate materials both above and below the tissue As shown in FIG. 4B, according to one embodiment, two anchors 61, 62 can be utilized where each anchor has an attached suture, and each attached suture has one limb 61' advancing though tissue only and a second limb 61" advancing through tissue and the scaffold 90. Each suture can be knotted on top of the scaffold 90 above the anchor site. In one embodiment, a single anchor and suture is used, having one limb 61' advancing though tissue only and a second limb 61" advancing through tissue and the scaffold 90. In one embodiment, a single anchor and suture is used, having both limbs 61', 61" advancing though tissue and the scaffold 90.

Figure 4C:
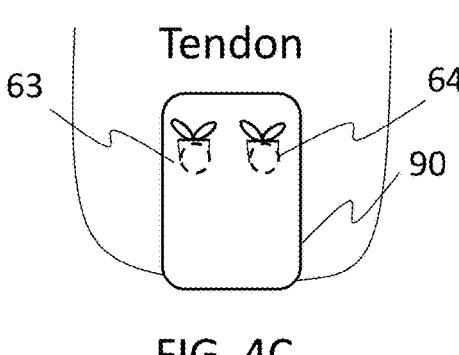

As shown in FIG. 4C, according to one embodiment, two anchors 63, 64 can be utilized where each anchor has an attached suture knotted on top of the scaffold 90 above the anchor site. Each attached suture can have both limbs advancing though tissue and the scaffold 90. In one embodiment, a single anchor and suture is used where both limbs of the suture advance through tissue and the scaffold.

Figure 4D:
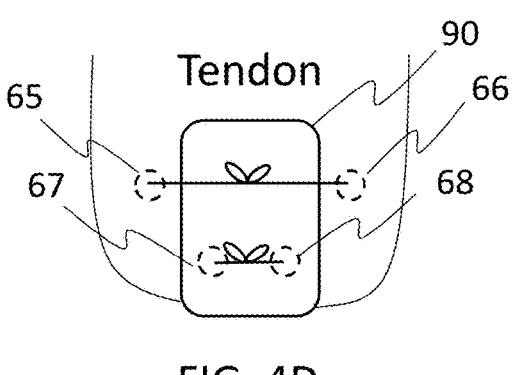

As shown in FIG. 4D, two anchors 65, 66 can be used to connect suture ends, bridging a suture by knotting it over the scaffold 90 according to one embodiment. One bridge can connect a medial row of anchors 65, 66 while a second bridge can connect a lateral row of anchors 67, 68. In one embodiment, at least one the anchors 65, 66 are outside the footprint of the scaffold 90. In one embodiment, both anchors 65, 66 are outside the footprint of the scaffold 90. In one embodiment, both anchors 67, 68 are inside the footprint of the scaffold. In one embodiment, one anchor can be inside the footprint of the scaffold while the other anchor is outside the footprint of the scaffold 90. In one embodiment, suture ends from different rows can be knotted together to form bridges between rows.

Figure 4E:
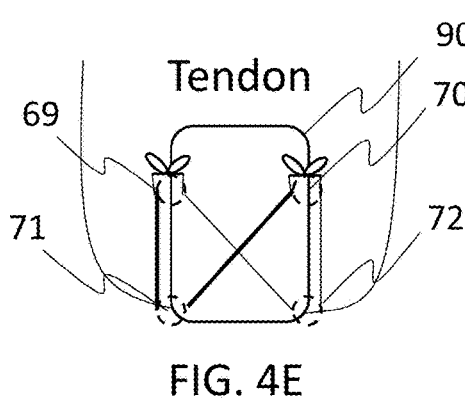

As shown in FIG. 4E, a row of knotted medial anchors 69, 70 can be combined with a row of knotless lateral anchors 71, 72 according to one embodiment. The row of knotted medial anchors 69, 70 can be positioned near the edge of the scaffold 90 so that one suture limb from the anchor advances through the tissue only while the other suture limb advances through the tissue and the scaffold. Similarly, the row of knotless lateral anchors 71, 72 can be positioned near the edge of the scaffold 90 and can accept sutures from above and diagonally for distributing a downward tension on the scaffold 90 and the tissue. One or more anchors can be positioned outside the footprint of the scaffold 90, inside the footprint of the scaffold 90, traversing an edge of the scaffold 90, or a combination of these configurations.

Figure 4F:
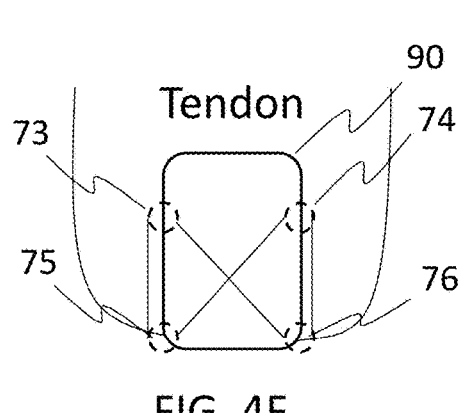

As shown in FIG. 4F, knotless anchors 73, 74, 75, 76 can be used for all anchoring points according to one embodiment. Accordingly, a row of knotless medial anchors 73, 74 is combined with a row of knotless lateral anchors 75, 76. Each anchor can accept a suture from the same row or a different row, directly adjacent or diagonally. Each anchor can be positioned near the edge of the scaffold 90 so that one suture limb from the anchor advances through the tissue only while the other suture limb advances through the tissue and the scaffold. In one embodiment, at least one of the rows has anchors within the scaffold 90 footprint. In one embodiment, at least one of the rows has anchors outside the scaffold 90 footprint.

Figure 4G:
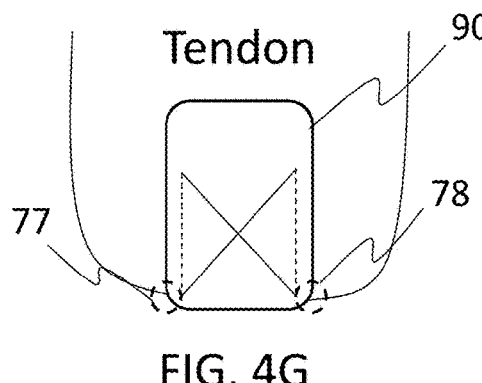

As shown in FIG. 4G, the scaffold and tissue can anchor to a single row of lateral anchors 77, 78 only, according to one embodiment. The lateral anchors 77, 78 can be knotless and positioned near the edge of the scaffold 90 and the tip of the tissue so that one suture limb from the anchor advances through the tissue only while the other suture limb advances through the tissue and the scaffold. Alternatively, both suture limbs can be inside or outside the scaffold's footprint. In one embodiment, the suture from each anchor is positioned diagonally across the scaffold, advancing down into the scaffold then connecting to the adjacent anchor.

Figure 4H:
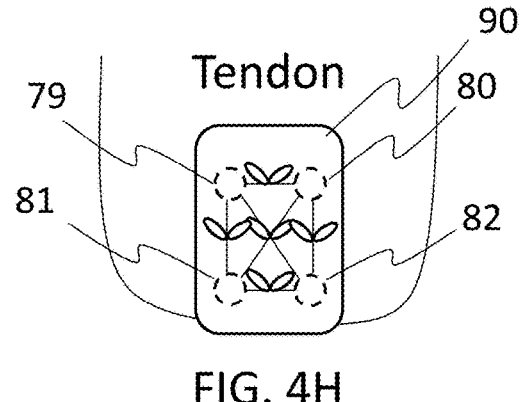

As shown in FIG. 4H, anchor bridges connecting a set of anchors 79, 80, 81, 82 can be utilized to anchor the scaffold and tissue according to one embodiment. The anchor bridges can connect sutures from the same row, adjacent from a different row, and diagonally. These combinations can all be implemented at the same time as depicted, or alternatively only certain combinations may be implemented. In one embodiment, the anchors are internal to the footprint of the scaffold 90. In one embodiment, the anchors are external to the footprint of the scaffold 90. In one embodiment, one row of anchors is external to the footprint of the scaffold 90 and the other row of anchors is internal to the footprint of the scaffold 90.

Figure 4I:
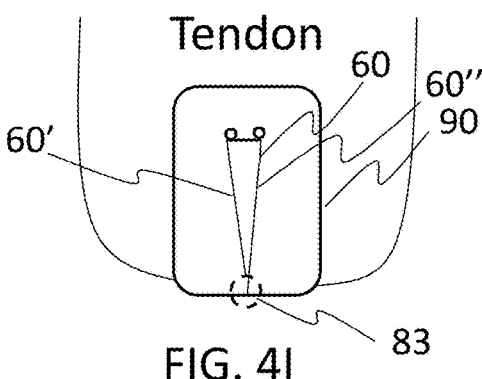
Figure 4J:
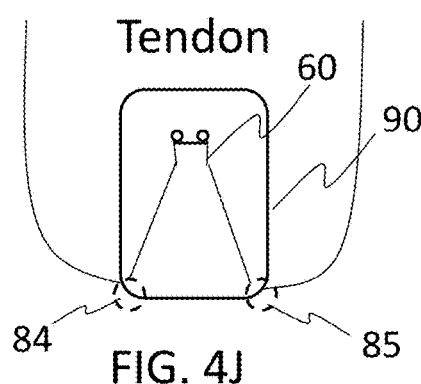

As shown in FIGS. 4I and 4J, according to certain embodiments, once the scaffold 90 is attached to the tissue by placement of a suture 60, one or more free ends of the suture can connect directly to an anchor. For example, the embodiment of FIG. 4I shows according to one embodiment a suture 60 connecting the scaffold 90 to the tissue, and first and second free ends 60', 60" of the suture 60 connected to a knotless anchor 83. Multiple anchors can be used in certain embodiments. For example, as shown in the embodiment of FIG. 4J, the suture 60 connects the scaffold 90 to tissue, and first and second free ends 60', 60" of the suture 60 connect to separate knotless anchors 84, 85. Additional connections such as a bridged connection between the knotless anchors 84, 85 can be implemented. As with previous embodiments, at least one limb of the suture should pass through the scaffold.

Figure 5:
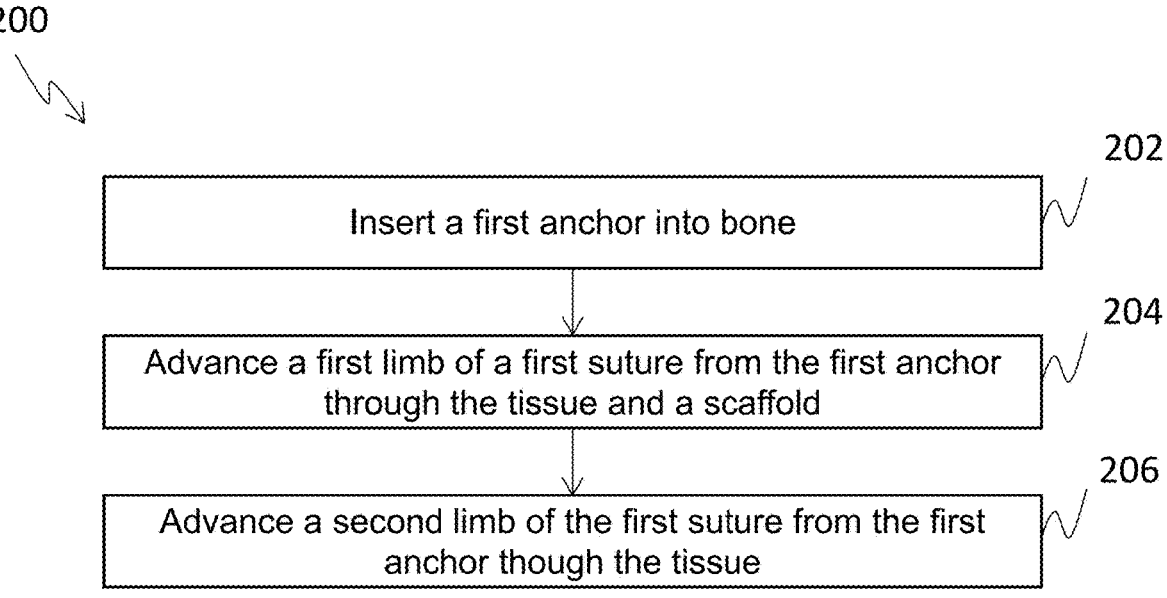
FIG. 5 is a flow chart of a method for attaching tissue to bone according to one embodiment.

Accordingly, in one embodiment with reference now to FIG. 5, a method 200 for attaching tissue to bone includes the steps of inserting a first anchor into bone 202; advancing a first limb of a first suture from the first anchor through the tissue and a scaffold 204; and advancing a second limb of the first suture from the first anchor though the tissue 206.

Figure 6:
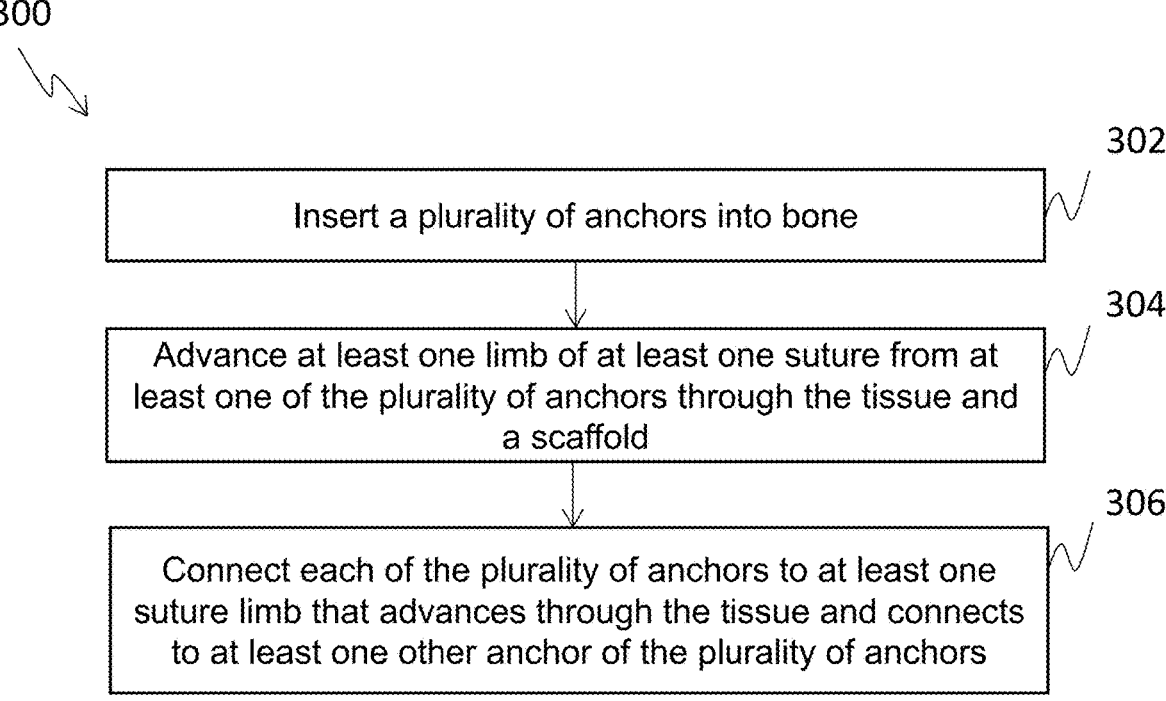
FIG. 6 is a flow chart of a method for attaching tissue to bone according to one embodiment.

In one embodiment with reference now to FIG. 6, a method 300 for attaching tissue to bone includes the steps of inserting a plurality of anchors into bone 302; advancing at least one limb of at least one suture from at least one of the plurality of anchors through the tissue and a scaffold 304; and connecting each of the plurality of anchors to at least one suture limb that advances through the tissue and connects to at least one other anchor of the plurality of anchors 306.

Figure 7:
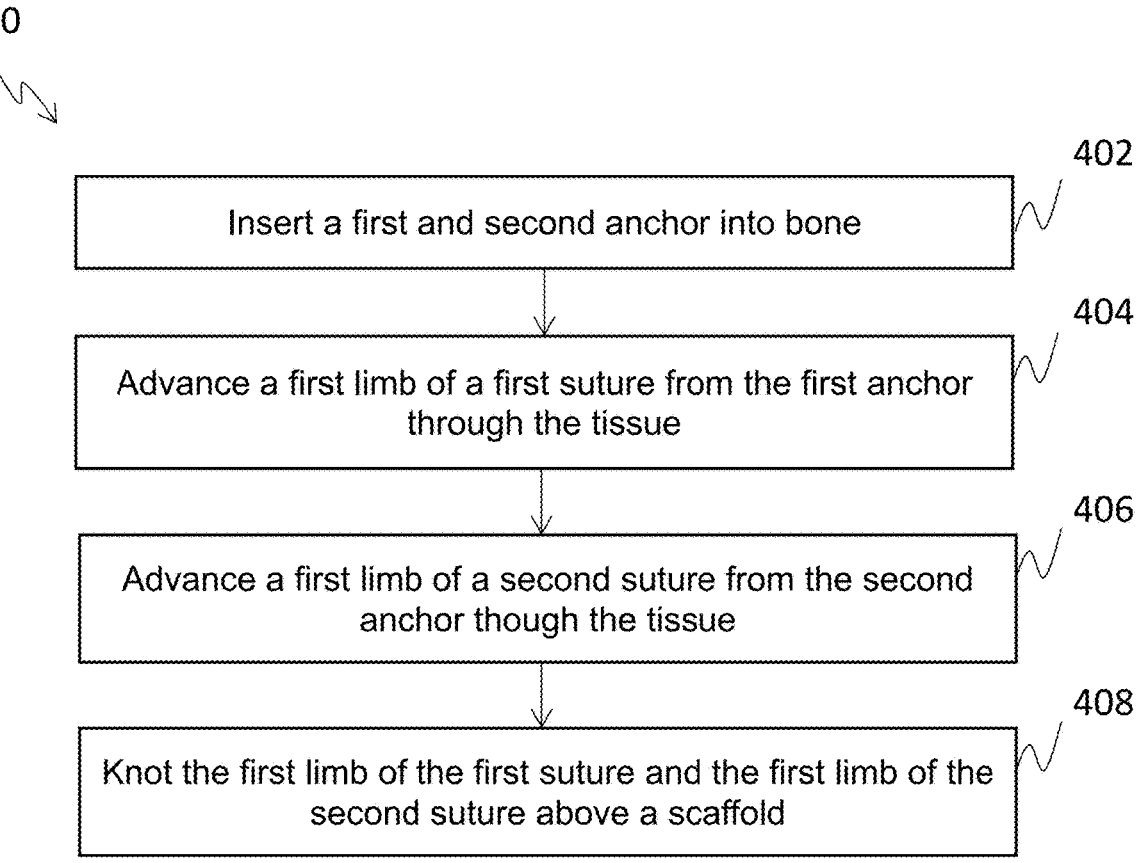
FIG. 7 is a flow chart of a method for attaching tissue to bone according to one embodiment.

In one embodiment with reference now to FIG. 7, a method 400 for attaching tissue to bone includes the steps of inserting a first and second anchor into bone 402; advancing a first limb of a first suture from the first anchor through the tissue 404; advancing a first limb of a second suture from the second anchor though the tissue 406; and knotting the first limb of the first suture and the first limb of the second suture above a scaffold 408.

Figure 8:
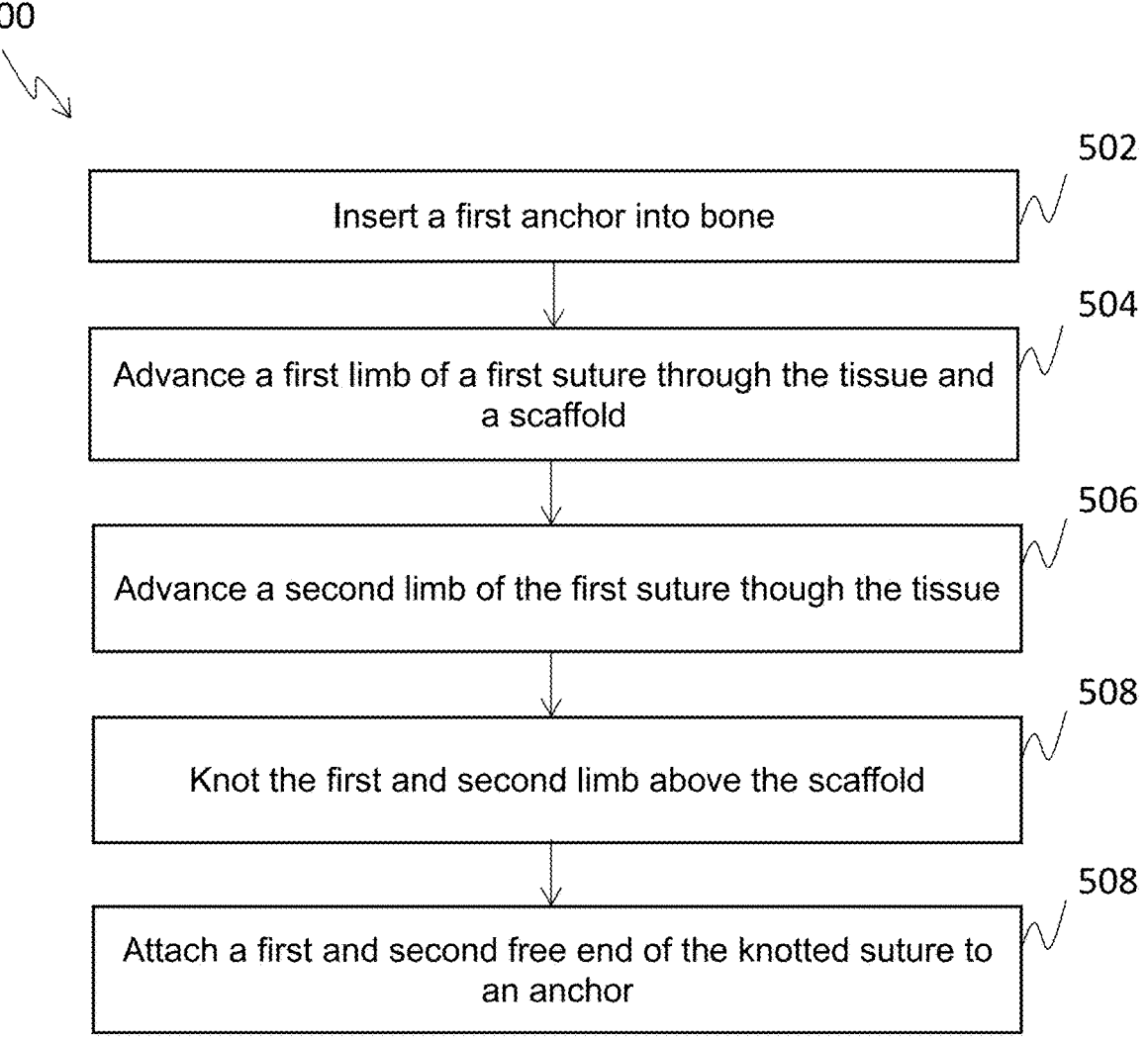
FIG. 8 is a flow chart of a method for attaching tissue to bone according to one embodiment.

In one embodiment with reference now to FIG. 8, a method 500 for attaching tissue to bone includes the steps of inserting a first anchor into bone 502; advancing a first limb of a first suture through the tissue and a scaffold 504; advancing a second limb of the first suture though the tissue 506; knotting the first and second limb above the scaffold 508; and attaching a first and second free end of the knotted suture to an anchor 510. In one embodiment, the first and second free end of the knotted suture are attached to the same anchor. In one embodiment, the first and second free end of the knotted suture are attached different anchors.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method for attaching tissue to bone comprising:
inserting a first anchor into a bone;
advancing a first limb of a first suture from the first anchor through the tissue and a scaffold, wherein the scaffold is positioned below the tissue; and
advancing a second limb of the first suture from the first anchor through the tissue.

2. The method of claim 1, wherein the second limb of the first suture is not advanced through the scaffold.

3. The method of claim 1, wherein the second limb of the first suture is advanced through the scaffold.

4. The method of claim 1, wherein the first and second limb of the first suture are knotted above the scaffold.

5. The method of claim 1, wherein the first anchor is positioned interior to a footprint of the scaffold.

6. The method of claim 1, wherein the first anchor is positioned exterior to a footprint of the scaffold.

7. The method of claim 1, wherein the first anchor is positioned traversing an edge of the scaffold.

8. The method of claim 1 further comprising:
inserting a second anchor into the bone;
advancing a first limb of a second suture from the second anchor through the tissue and the scaffold; and
advancing a second limb of the second suture from the second anchor through the tissue.

9. The method of claim 8, wherein the second limb of the second suture is not advanced through the scaffold.

10. The method of claim 8, wherein the second limb of the second suture is advanced through the scaffold.

11. The method of claim 8, wherein the first and second limb of the second suture are knotted above the scaffold.

12. The method of claim 8, wherein the second anchor is positioned interior to a footprint of the scaffold.

13. The method of claim 8, wherein the second anchor is positioned exterior to a footprint of the scaffold.

14. The method of claim 8, wherein the second anchor is positioned traversing an edge of the scaffold.

15. The method of claim 1, wherein the scaffold is positioned above the tissue.

16. The method of claim 1, wherein the scaffold wraps around a tip of the tissue and is positioned both above and below the tissue.

17. A method for attaching tissue to bone comprising:
inserting a first anchor into a bone;
advancing a first limb of a first suture from the first anchor through the tissue and a scaffold, wherein the scaffold wraps around a tip of the tissue and is positioned both above and below the tissue; and
advancing a second limb of the first suture from the first anchor through the tissue.

18. The method of claim 17, wherein the second limb of the first suture is not advanced through the scaffold.

19. The method of claim 17, wherein the second limb of the first suture is advanced through the scaffold.

20. The method of claim 17, wherein the first and second limb of the first suture are knotted above the scaffold.

21. The method of claim 17, wherein the first anchor is positioned interior to a footprint of the scaffold.

22. The method of claim 17, wherein the first anchor is positioned exterior to a footprint of the scaffold.

23. The method of claim 17, wherein the first anchor is positioned traversing an edge of the scaffold.

24. The method of claim 17 further comprising:
inserting a second anchor into the bone;
advancing a first limb of a second suture from the second anchor through the tissue and the scaffold; and
advancing a second limb of the second suture from the second anchor through the tissue.

25. The method of claim 24, wherein the second limb of the second suture is not advanced through the scaffold.

26. The method of claim 24, wherein the second limb of the second suture is advanced through the scaffold.

27. The method of claim 24, wherein the first and second limb of the second suture are knotted above the scaffold.

28. The method of claim 24, wherein the second anchor is positioned interior to a footprint of the scaffold.

29. The method of claim 24, wherein the second anchor is positioned exterior to a footprint of the scaffold.

30. The method of claim 24, wherein the second anchor is positioned traversing an edge of the scaffold.

31. The method of claim 17, wherein the scaffold is positioned above the tissue.

* * * * *